United States Patent [19]

Itakura

[11] 4,373,071
[45] Feb. 8, 1983

[54] SOLID-PHASE SYNTHESIS OF POLYNUCLEOTIDES

[75] Inventor: Keiichi Itakura, Arcadia, Calif.

[73] Assignee: City of Hope Research Institute, Duarte, Calif.

[21] Appl. No.: 258,925

[22] Filed: Apr. 30, 1981

[51] Int. Cl.³ .............................................. C08F 8/40
[52] U.S. Cl. .................................. 525/375; 525/340; 536/28; 536/29; 536/23; 536/24
[58] Field of Search ...................... 525/366, 340, 375; 521/32; 536/22, 23, 24, 25, 26, 27, 28, 29

[56] References Cited

U.S. PATENT DOCUMENTS

| | | | |
|---|---|---|---|
| 3,985,690 | 10/1976 | Dean | 536/22 |
| 4,037,037 | 7/1977 | Patchovnik et al. | 525/366 |
| 4,043,948 | 8/1977 | Rayskys et al. | 525/366 |
| 4,066,827 | 1/1978 | Seita | 525/375 |
| 4,217,421 | 8/1980 | Beasley | 521/32 |
| 4,276,395 | 6/1981 | Vollhardt et al. | 525/366 |

OTHER PUBLICATIONS

Itakura et al., Tetrahedron Letters No. 38, pp. 3635–3638, 1979.

Primary Examiner—Paul R. Michl
Attorney, Agent, or Firm—Ellsworth R. Roston; Charles H. Schwartz

[57] ABSTRACT

A commercially available resin such as polystyrene is converted into a phthalimidomethyl-resin by treatment with potassium phthalimide. The phthalimidomethyl-resin is converted into an amino resin with hydrazine in ethanol. The amino resin is then combined with an activated ester of a nucleoside to obtain an amide-bonded dimethoxytrityl resin. The activated ester of the nucleoside is obtained by reacting a nucleoside with succinic anhydride in the presence of 4-(dimethylamino) pyridine in pyridine to provide a monosuccinate derivative, which is in turn treated with pentachlorophenol and dicyclohexylcarbodimide in dimethylformamide. Any unreacted amino groups in the amide-bonded dimethoxytrityl resin may be masked and the dimethoxytrityl group may be removed by treatment of the amide-bonded resin with a solution of benzenesulfonic acid to obtain a hydroxylated resin support. Additional mononucleotides, dinucleotides and trinucleotides may be added to the resin support in the presence of a coupling reagent such as 2,4,6-triisopropylbenzenesulfonyl tetrazolide. Any unreacted 5′-hydroxyl group may be masked with acetic anhydride. The steps described in the previous two sentences may be repeated to form polynucleotides of any desired sequence. The resin may also be a polyacrylmorpholide. This resin may be converted into an amino resin with ethylene diamine in ethylene glycol. The resin may also be a silica gel. The silica gel may be treated by any of the above methods, to provide a solid-phase resin support for the nucleotides.

44 Claims, 4 Drawing Figures

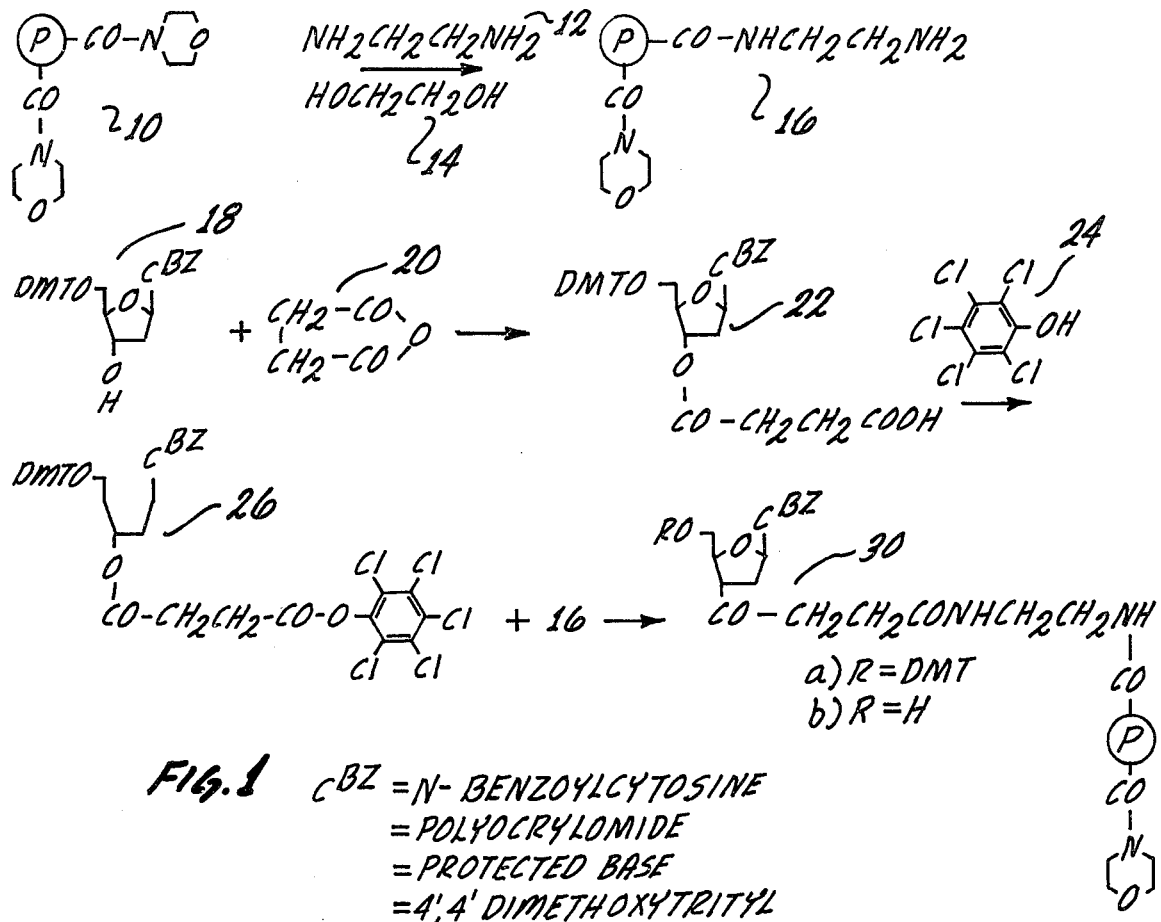
Fig. 1   $C^{BZ}$ = N- BENZOYLCYTOSINE
 = POLYOCRYLOMIDE
 = PROTECTED BASE
 = 4',4' DIMETHOXYTRITYL
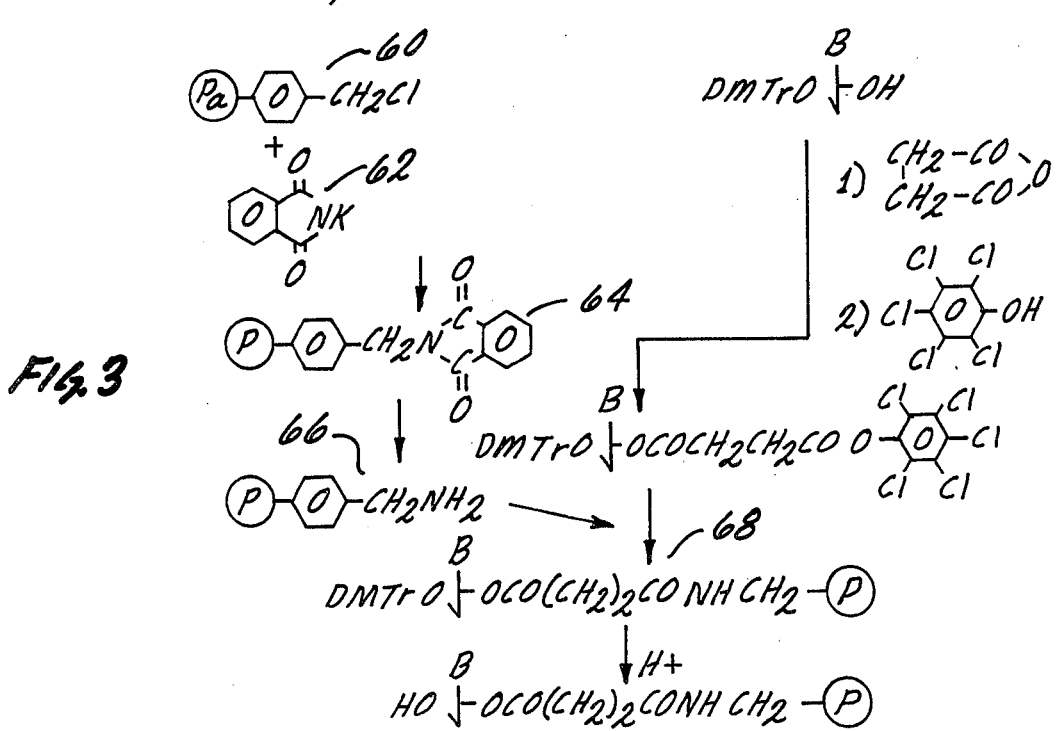
Fig. 3

| STEP | SOLVENT OR REAGENT | AMOUNT | SHAKING TIME | NUMBER OF OPERATIONS |
|---|---|---|---|---|
| 1 | PYRIDINE | 10 ml | 1 | 2 |
| 2 | 10% SOLUTION $(CH_3CO)_2O$ IN PYRIDINE | 10 ml | 60 | 1 |
| 3 | PYRIDINE | 10 ml | 1 | 2 |
| 4 | $CHCl_3$-MeOH (7:3 v/v) | 10 ml | 1 | 3 |
| 5 | 2% BSA | 10 ml | 0.5 | 2 |
| 6 | $CHCl_3$-MeOH (7:3 v/v) | 10 ml | 1 | 2 |
| 7 | PYRIDINE | 10 ml | 1 | 2 |
| 8 | DIMER OR TRIMER IN PYRIDINE | 5 EQUIVALENT | CO-EVAPORATION | 1 |
| 9 | TPST IN PYRIDINE | 10 EQUIVALENT /5ml | 120 | 1 |

4,373,071

SOLID-PHASE SYNTHESIS OF POLYNUCLEOTIDES

This invention relates to methods of producing nucleotides, including polynucleotides, in a relatively simple and efficient manner. The invention also relates to resin supports and to polynucleotides produced by such methods.

The synthesis of polynucleotides has become important in recent years in the synthesis of DNA. By such synthesis of DNA, life-saving chemicals such as insulin can be formulated artificially. Such artificial formulations will provide for a more efficient production of the materials than the chemicals of the prior art. Other materials will hopefully also be formulated for the benefit of mankind by restructuring the DNA.

In order to synthesize the DNA, polynucleotides of particular formulation often have to be provided. These polynucleotides often have had to be formulated through progressive cycles of chemical reactions. In the first such cycle, a mononucleoside has been provided. In subsequent cycles, mononucleotides, dinucleotides or trinucleotides have been added to the mononucleoside. The addition of the mononucleotides, dinucleotides and trinucleotides to the mononucleoside in each cycle has been relatively slow and inefficient.

Attempts have also been made in the prior art to add nucleotides to solid phase supports. Such attempts have not been successful because the chemistry has not been adequate to provide successful chemical reactions, particularly in converting the solid-phase resin to a mononucleoside for receiving the successive nucleotides. The advantage of providing a solid-phase support is that the support can easily be separated from the solution. This enhances considerably the speed at which the different chemical reactions can be accomplished.

In a paper published by Keiichi Itakura and Ken-ichi Miyoshi in 1979, more than one (1) year prior to the filing date of this patent application, a method is disclosed of providing a solid support (specifically, a polyacrylmorpholide) which is easily separated from the solution. This paper is entitled "Solid Phase Synthesis of Nonadecathymidylic Acid By the Phosphotriester Approach" and is printed from Tetrahedron Letters No. 38, pp. 3635–3638, published by Pergamon Press Ltd. This paper also discloses a method of reproducing a polynucleotide or a carboxylic derivative of such support. However, all of the nucleotides described in the paper as being included in the polynucleotide are a thymidilic acid. By providing a solid support which is easily separated from the solution, the production of nucleotides containing thymidilic acids is greatly facilitated.

Since the publication in 1979 of the paper described in the previous paragraph, the solid-phase synthesis of polynucleotides with defined sequences has been provided. One solid-phase support for such polynucleotides has been a polyacrylmorpholide resin. The polyacrylmorpholide resin has been converted into an amino-resin by reaction with ethylene diamine in ethylene glycol. The production of such amino-resins constitutes one of the features of this invention. Such amino-resins have then provided the support for sequences of nucleotides. The nucleotides in such sequences have included quanine, adenine and cystosine acids as well as the thymidilic acids.

Another feature of this invention is the method of attaching sequences of nucleotides to the amino-resin. This is accomplished by combining the amino-resin with an activated ester of a nucleoside to obtain an amide-bonded dimethoxytrityl resin. The actived ester of the nucleoside is obtained by reacting a nucleoside with succinic anhydride in the presence of 4-(dimethylamino) pyridine in pyridine to provide a monosuccinic derivative, which is in turn treated with pentachlorophenol and dicyclohexylcarbodimide in dimethylformamide.

To prepare the amide-bonded dimethoxytrityl resin for the coupling of additional nucleotides, any unreacted amino group in the resin may be masked and the dimethoxytrityl group may be removed by treatment of the amide-bonded resin with a solution of benzenesulfonic acid to obtain a hydroxylated resin support. Additional mononucleotides, dinucleotides and trinucleotides may then be added to the resin support in the presence of a coupling reagent such as 2,4,6-triisopropylbenzenesulfonyl tetrazolide. Any unreacted 5'-hydroxyl group may be masked with acetic anhydride. The steps described in the previous two sentences may be repeated to form polynucleotides of any desired sequence. The method described in these paragraphs of adding nucleotides to a resin support also constitutes one of the features of this invention.

The invention also involves the use of polystyrene as a solid-phase support. Polystyrene is advantageous as a solid-phase support in comparison to a polyacrylmorpholide because it has no problems of affinity to hydroxylic groups such water, methanol and ethanol. To convert the polystyrene into a solid-phase resin support for nucleotides, a commercially available polystyrene is converted into a phthalimidomethyl-resin by treatment with potassium phthalimide. The phthalimidomethyl-resin is then converted into an amino resin with hydrazine in ethanol. Chlorophenolated nucleosides may then be attached to the amino resin in a manner similar to that described above.

In addition to a polyacrylmorpholide and a polystyrene, a silica gel may also be used as the resin. The silica gel may be treated by any of the above methods to provide a solid-phase resin support for the nucleotides.

In the drawings:

FIG. 1 illustrates the steps providing a polyacrylmorpholide support and attaching a first nucleoside to such resin support;

FIG. 3 illustrates a method of providing a polystyrene support and attaching a first nucleoside to such resin support.

Figures 2, 4:
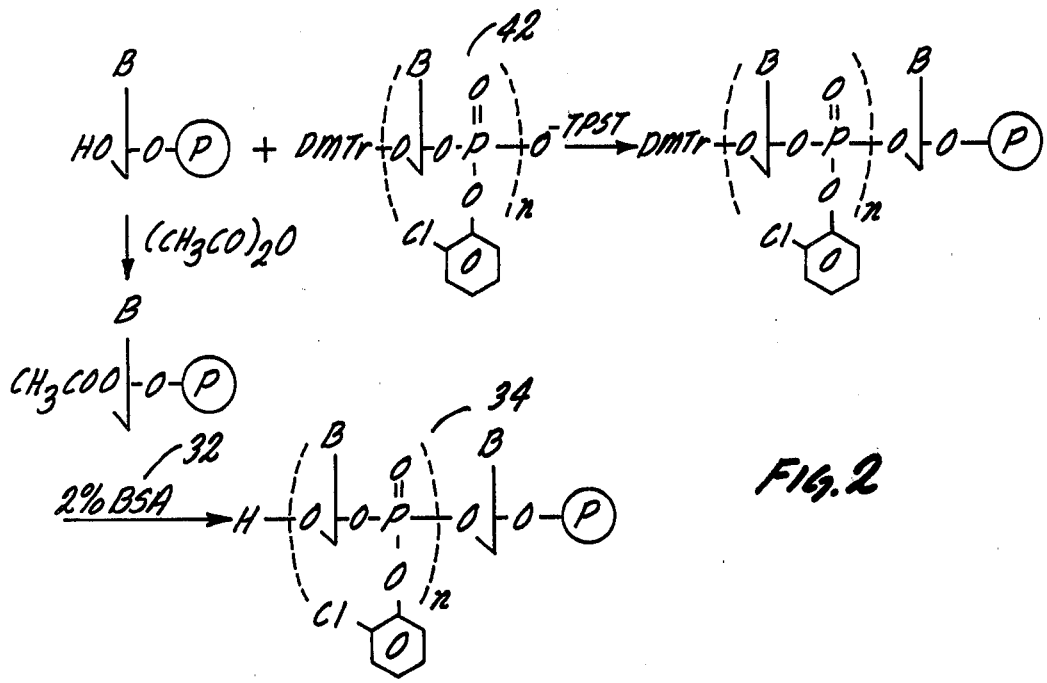
FIG. 2 illustrates the steps of attaching mononucleotides, dinucleotides and trinucleotides to the resin support after the first nucleoside has been attached to the resin support.
FIG. 4 is a table of successive steps involved in preparing a resin support for the attachment of additional nucleotides to the resin support after the first nucleoside has been attached to the resin support.

In one embodiment of the invention, a polyacrylmorpholide resin 10 may be used as a solid-phase support for a polynucleotide. The polyacryhmorpholide resin 10 may be commercially available Enzacryl Gel K-2 resin marketed by the Aldrich Chemical Company. Such a commercially available resin may be derivatized with ethylenediamine 12 in ethylene glycol 14 to form an amino-resin 16 (0.20 mmole/g of the amino function).

A 5'-0-dimethoxytrityl deoxynucleoside 18 may be reacted with succinic anhydride 20 (1.5 mol equivalent) in the presence of 4-(dimethylamino) pyridine (1.5 mol equivalent) in pyridine at a suitable temperature for an extended period such as overnight to provide a monosuccinate derivative 22 in a yield of approximately eighty percent (80%). The monosuccinate derivative 22 may be treated with pentachlorophenol 24 (1.1 mol equivalent) and dicyclohexylcarbodimide (3 mol equivalent) in dimethylformamide at a suitable temperature such as room temperature for an extended time such as approximately twenty (20) hours to form an activated ester 26 of the nucleoside in a yield of approximately ninety percent (90%).

The amino-resin 16 may be treated with the activated ester 26 of the nucleoside (2.5 mol equivalent) and triethylamine (2.75 mol equivalent) in dimethylformamide to provide an amino-bonded dimethoxytrityl resin 30. The formation of this resin may be facilitated by shaking the mixture at a suitable temperature such as room temperature for an extended period such as approximately twenty (20) hours.

Any unreacted amino group in the resin 30 may be masked by treatment with phenylisocyanate (10% solution in pyridine) at a suitable temperature such as room temperature for a suitable time such as approximately one (1) hour. The dimethoxytrityl group may then be removed by treatment with a two percent (2%) solution of benzenesulfonic acid 32 (FIG. 2) in $CHCl_3$—MeOH (7:3 v/v) at a suitable temperature such as room temperature for a relatively short time such as approximately thirty (30) seconds. In this way, a nucleoside 34 is obtained. The nucleoside serves as a support for the attachment of additional nucleotides by one of the methods of this invention to form a polynucleotide.

The method described above is disclosed in detail in the following article prepared by scientists who were employees of the assignee of record of this patent application at the time that such article was published:

Solid-phase synthesis of hentriacontanucleotide by Pietr Dembek, Ken-ichi Miyoshi and Keiichi Itakura.

This article was published in Journal of the American Chemical Society in 1981 at Volume 103, pages 706–708.

FIG. 4 indicates the modifications of the removal condition of the dimethoxytrityl group from the nucleoside 34. The support may be initially washed with pyridine, as shown in step 1 of FIG. 4, and the 5'-hydroxyl group may then be masked with a ten percent (10%) solution of acetic anhydride, as shown in step 2 of FIG. 4. The resin support may then be washed with pyridine (Step 3 of FIG. 4) and may be subsequently washed a particular number of times (such as 3 times) with a $CHCl_3$-MeOH (7:3 v/v) solution which has been pre-cooled to a suitable temperature such as 0° C. This has been shown in Step 4 of FIG. 4. The dimethoxytrityl resin may be shaken with the pre-cooled solution of $CHCl_3$MeOH to cool and swell the resin.

The resin support is then treated with a two percent (2%) solution of benzenesulfonic acid in $CHCl_3$—MeOH (7:3 v/v, 10 ml). This treatment is shown in Steps 5 and 6 of FIG. 4. The treatment may occur for a suitable period of time such as approximately one (1) minute under a vigorous shaking. The nucleoside may then be washed in a suitable material such as pyridine. Such washing is illustrated in Steps 7 and 8 of FIG. 4. By this procedure, the dimethoxytrityl group is completely removed without harming the adenine residue in the oligonucleotide.

Step 9 of FIG. 4 illustrates in a concise form the method of applicants for adding nucleotides to the resin support 30 to obtain a polynucleotide. In this step, "TPSTe" in FIG. 4 is intended to mean 2,4,6-triisopropylbenzenesulfonyl tetrazolide. In this step, the 2,4,6-triisopropylbenzenesulfonyl tetrazolide (15 mol equivalent) and anhydrous pyridine (8 ml) are added to the residue from Step 8 and the appropriate nucleotides to be coupled to the resin support are also added to the mixture. The reaction mixture is then shaken and filtered. This step is also shown in FIG. 2 wherein the appropriate nucleotide is designated at 40.

Various polynucleotides have been formed by the method described above. For example, a hentriacontanucleotide containing the sequence d(TGGTGCACCTGACTCCTGAG-GAGAAGTCTGC) has been formed by the method described above. Actually, however, it has been found that the polystyrene often serves as a more favorable resin support than the polyacrylmorpholide. This results from the relative affinity of the polyacrylmorpholide support to hydroxylic groups such as water, methanol and ethanol. The relative affinity of the polyacrylmorpholides to such hydroxylic groups tends to inhibit the coupling of the nucleotides to the resin support. This affinity tends to inhibit any automation of the operation of preparing polynucleotides from a resin support.

When polystrene is used as the resin support, Merrifield polystyrene (1% or 2% cross-linked by divinylbenzene) has been found to be preferable. One reason is that the coupling efficiency to form phosphotriester bonds on such a resin is relatively high and is actually as high as on the polyacrylmorpholide resin.

FIG. 3 illustrates a method of coupling a first nucleoside to a polystyrene to provide the resin support. In this method, commercially available chloromethylpolystyrene 60 (1.06 mmole of Cl(CHlorine)/g) is converted into a phthalimidomethyl-resin 64 by treatment with potassium phthalimide 62. The phthalimidomethyl-resin 64 is then converted into an amino resin 66 with hydrazine in ethanol. The procedure to attach the first nucleoside to the amino resin 66 is described above and shown in FIG. 1 for coupling to the polyacrylmorpholide. The amino-bonded dimethoxytrityl polystyrene-resin produced by reaction of the amino-resin 66 with the activated ester of the nucleoside is illustrated at 68 in FIG. 2.

The method shown in FIG. 2 and described above is fully disclosed in an article entitled "Solid-phase synthesis of polynucleotide.IV. Usage of polystyrene resins for the synthesis of polydeoxyribonucleotide by the phosphotriester method." This article was prepared by Ken-ichi Miyoshi, Rene Arentzen, Ting Huang and Keiichi Itakura, who were at that time employees of the assignee of record of this application. The article was published in Nucleic Acids Research at Volume 8 Number 22 1980.

The methods described above are also advantageous when used with silica gel as the resin support. Silica gel is advantageous as a resin support because it does not swell when mixed with various solvents. Silica gel is also advantageous because the reactions with silica gel tend to occur at a relatively fast rate.

Although this application has been disclosed and illustrated with reference to particular applications, the principles involved are susceptible of numerous other applications which will be apparent to persons skilled in the art. The invention is, therefore, to be limited only as indicated by the scope of the appended claims.

I claim:

1. In a method of creating polynucleotides, the following steps:
   treating a resin with potassium phthalimide to obtain a phthalimidomethyl-resin,
   converting the phthalimidomethyl-resin into an amino resin with hydrazine, and
   combining the amino-resin with an activated ester of a nucleoside to obtain an amino-bonded dimethoxytrityl resin.

2. The method set forth in claim 1 wherein
   the activated ester of the nucleoside is obtained
   by reacting a nucleoside with succinic anhydride to provide a monosuccinic derivative and
   by treating the monosuccinic derivative with pentachlorophenol.

3. The method set forth in claim 2 wherein
   the resin is selected from a group consisting of silica gel and polystyrene.

4. The method set forth in claim 3 wherein
   the nucleoside is reacted with succinic anhydride in the presence of 4-dimethylamino pyridine to provide the monosuccinic derivative and
   the monosuccinic derivative is treated with pentachloraphenol and dicyclohexyl carbodimide in dimethyl formamide to obtain the activated ester of the nucleoside.

5. A method of creating polynucleotides, including the following steps;
   converting a resin into an amino-resin;
   combining the amino-resin with a chlorophenolated nucleoside to obtain an amino-bonded dimethoxytrityl resin support, and
   hydroxylating the dimethoxytrityl group in the amino-bonded resin support to provide for the coupling of nucleotides to the resin support.

6. The method set forth in claim 5 wherein
   additional nucleotides are added to the hydroxylated amino-bonded resin support in the presence of a coupling reagent and
   any unreacted 5'-hydroxyl group in the amino-bonded resin support is masked before the additional nucleotides are added to the hydroxylated amino-bonded resin support.

7. The method set forth in claim 6 wherein
   the coupling reagent for adding the nucleotides to the hydroxylated amino-bonded resin support is 2,4,6-triisopropylbenzenesulfonyl tetrazolide and
   and any unreacted 5'-hydroxyl group in the amino-bonded resin support is masked with acetic anhydride before the additional nucleotides are added to the hydroxylated amino-bonded resin support.

8. The method set forth in claim 7 wherein
   the resin is selected from a group consisting of silica gel and polystyrene and
   the resin is treated with potassium phthalimide to obtain a phthalimidomethyl-resin and
   the phthalimidomethyl-resin is converted into the amino-resin with hydrazine.

9. The method set forth in claim 7 wherein
   the dimethoxytrityl group in the amino-bonded resin support is hydroxylated with a solution of benezenesulphonic acid.

10. The method set forth in claim 6 wherein
    the resin constitutes a polyacrylmorpholide and the resin is converted into the amino-resin with ethylenediamine in ethylene glycol.

11. A method of creating a polynucleotide, including the following steps:
    (a) providing a resin,
    (b) applying chemicals containing amino radicals to the resin to obtain an amino-resin,
    (c) converting the amino-resin into an amino-bonded dimethoxytrityl resin support,
    (d) hydroxylating the dimethoxytrityl group in the resin support, and
    (e) coupling nucleotides to the hydroxylated resin support.

12. A method as set forth in claim 11 wherein
    the nucleotides are added to the hydroxylated resin support in the presence of a coupling reagent and any unreacted 5'-hydroxyl group in the resin support is masked.

13. A method set forth in claim 12 wherein
    the steps (d) and (e) of claim 12 are repeated to couple additional nucleotides to the polynucleotide.

14. A method set forth in claim 13 wherein
    the coupling reagent is 2,4,6-triisopropyl benzenesulfonyl tetrazolide and
    any unreacted 5'-hydroxyl group in the amino-bonded resin support is masked with acetic anhydride before the nucleotides are coupled to the resin support.

15. A method set forth in claim 13 wherein
    the resin is a polyacrylmorpholide and
    the resin is converted to the amino-resin with ethylenediamine in the presence of ethylene glycol.

16. A method as set forth in claim 13 wherein
    the resin is selected from a group consisting of silica gel and polystyrene, and
    the resin is converted into a phthalimidomethyl-resin by treatment with potassium phthalimide, and
    the phthalimidomethyl-resin is converted to the amino-resin with hydrazine in ethanol.

17. A method as set forth in claim 17 wherein
    the amino-bonded resin support is treated with a solution of benzenesulphonic acid to hydroxylate the dimethoxytrityl group after the masking of the unreacted 5'-hydroxyl group in the amino-bonded resin support and before the nucleotides are coupled to the hydroxylated resin support.

18. A method of creating polynucleotides, including the following steps:
    providing a resin support,
    providing an activated ester of a nucleoside, and
    combining the activated ester of the nucleoside and the resin support to obtain a resin-supported nucleoside.

19. A method as set forth in claim 18, including the following steps:
    hydroxylating the dimethoxytrityl group in the resin-supported nucleoside and
    adding nucleotides to the hydroxylated resin-supported nucleoside to obtain a resin-supported polynucleotide.

20. A method as set forth in claim 19 wherein
    the dimethoxytrityl group in the resin-supported nucleotide is hydroxylated in the presence of a solution of a benzenesulfonic acid and wherein
    the nucleotides are added to the hydroxylated resin support in the presence of 2,4,6-triisopropylbenzenesulfonyl tetrazolide.

21. A method as set forth in claim 17 wherein
the resin in the resin support is selected from a group consisting of silica gel and polystyrene.

22. A method as set forth in claim 17 wherein the resin support is a polyacrylmorpholide.

23. A method set forth in claim 20 wherein
the activated ester of a nucleoside is provided by reacting a nucleoside with a succinic anhydride to provide a monosuccinate derivative and
treating the monosuccinate derivative with pentachlorophenol to produce the activated ester of the nucleoside.

24. A method of creating polynucleotides, including the following steps:
providing a resin,
converting the resin into an amino-resin,
providing a nucleoside,
combining the amino-resin and the nucleoside to obtain an amino-bonded dimethoxytrityl resin support,
hydroxylating the dimethoxytrityl group in the amino-bonded resin support, and
attaching nucleotides to the hydroxylated amino-bonded resin support.

25. A method set forth in claim 24 wherein
the resin is selected from a group consisting of a polyacrylmorpholide, a polystyrene and a silica gel.

26. A method set forth in claim 25 wherein
the dimethoxytrityl group in the amide-bonded resin support is hydroxylated by treatment with a solution of a benzenesulphonic acid and
the nucleotides are attached to the hydroxylated resin support in the presence of a coupling reagent constituting 2,4,6-triisopropylbenzenesulfonyl tetrazolide.

27. A method as set forth in claim 26 wherein
the resin is a polyacrylmorpholide and the resin is converted into an amino-resin with ethylenediamine in ethylene glycol.

28. A method as set forth in claim 26 wherein
the resin is selected from a group consisting of silica gel and a polystyrene and the resin is converted into a pthalimidomethyl-resin by treatment with potassium phthalimide and
the phthalimidomethyl-resin is converted into the amino resin with hydrazine in ethanol.

29. A method as set forth in claim 26 wherein
the resin is a silica gel and the resin is converted into a phthalimidomethyl-resin by treatment with potassium phthalimide and
the phthalimidomethyl-resin is converted into the amino resin with hydrazine in ethanol.

30. A method as set forth in claim 24 wherein
the nucleoside is converted into a chlorophenolated nucleoside and
the amino-resin and the chlorophenolated resin are combined to obtain the amide-bonded dimethoxytrityl resin support.

31. A method as set forth in claim 11 wherein steps (c) is provided as follows:
(f) providing a deoxynucleoside,
(g) treating the deoxynucleoside with succinic anhydride to provide a monosuccinate derivative,
(h) treating the monosuccinate derivative with pentachlorophenol to form an activated ester of the nucleoside, and (i) combining the amino-resin and the activated ester of the nucleoside to obtain the amino-bonded dimethoxytrityl resin support.

32. A method as set forth in claim 31 wherein
steps (d) and (e) are repeated to couple additional nucleotides in the polynucleotide.

33. A method as set forth in claim 31 wherein
the resin is a polyacrylmorpholide and
the resin is converted to the amino-resin with ethylene diamine in the presence of ethylene glycol.

34. A method as set forth in claim 31 wherein
the resin is selected from a group consisting of silica gel and polystyrene, and
the resin is converted into a pthalimidomethyl-resin by treatment with potassium phthalimide and
the phthalimidomethyl-resin is converted to the amino-resin with hydrazine in ethanol.

35. A method as set forth in claim 33 wherein
step (e) is provided by adding nucleotides to the hydroxylated resin support in the presence of 2,4,6-triisopropylbenezenesulfonyl tetrazolide.

36. A method as set forth in claim 34 wherein
step (e) is provided by adding nucleotides to the hydroxylated resin support in the presence of 2,4,6-triisopropylbenezenesulfonyl tetrazolide.

37. A method as set forth in claim 31 wherein
any unreacted 5'-hydroxyl group in the amino-bonded resin support is masked with acetic anhydride before the nucleotides are coupled to the resin support and
the nucleotides are added to the hydroxylated resin support in the presence of 2,4,6-triisopropyl-benezenesulfonyl tetrazolide.

38. A method of creating a polynucleotide, including the following:
(a) providing a deoxynucleoside,
(b) treating the deoxynucleoside with succinic anhydride to provide a monosuccinate derivative,
(c) treating the monosuccinate derivative with pentachlorophenol to form an activated ester of the nucleoside,
(d) providing an amino-resin
(e) combining the amino-resin and the activated ester of the nucleoside to obtain an amino-bonded dimethoxytrityl resin support,
(f) hydrozylating the dimethoxytrityl group in the resin support, and
(g) coupling nucleotides to the hydroxylated resin support.

39. A method as set forth in claim 38 wherein
the dimethoxytrityl group in the resin support is hydroxylated by treatment with benzenesulphonic acid.

40. A method as set forth in claim 38 wherein
the nucleotides are coupled to the hydroxylated resin support in the presence of a coupling agent constituting 2,4,6-triisopropylbenezenesulfonyl tetrazolide.

41. A method as set forth in claim 38 wherein
the resin in the amino-resin is selected from a group consisting of a polyacrylmorpholide, a polystyrene and a silica gel.

42. The method set forth in claim 40 wherein
the dimethoxytrityl group in the resin support is hydroxylated by treatment with a benezenesulphonic acid and
the nucleotides are coupled to the hydroxylated resin support in the presence of a coupling agent constituting 2,4,6-triisopropylbenezenesulfonyl tetrazolide.

43. The method set forth in claim 41 wherein
the resin in the amino-resin is selected from a group consisting of polystyrene and silica gel and
the resin is treated with potassium phthalimide to obtain a phthalimido methyl-resin and
the phthalimido methyl-resin is converted into the amino-resin with hydrazine.

44. The method set forth in claim 42 wherein
the resin constitutes a polyacrylmorphouide and
the resin is converted into the amino-resin with ethylenediamine in ethylene glycol.

* * * * *

Notice of Adverse Decisions in Interference

In Interference No. 101,724, involving Patent No. 4,373,071, Keiichi Itakura, SOLID-PHASE SYNTHESIS OF POLYNUCLEOTIDES, final judgement adverse to the patentee was rendered June 11, 1991, as to claims 1-44.

(*Official Gazette Oct. 22, 1991*)